United States Patent
Takahashi et al.

(10) Patent No.: US 9,572,546 B2
(45) Date of Patent: Feb. 21, 2017

(54) OBJECT INFORMATION ACQUIRING APPARATUS

(71) Applicant: CANON KABUSHIKI KAISHA, Tokyo (JP)

(72) Inventors: Hiroki Takahashi, Natori (JP); Hisafumi Ebisawa, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 13/803,601

(22) Filed: Mar. 14, 2013

(65) Prior Publication Data
US 2013/0267851 A1    Oct. 10, 2013

(30) Foreign Application Priority Data
Apr. 5, 2012   (JP) ................. 2012-086209

(51) Int. Cl.
*A61B 8/00*  (2006.01)
*A61B 8/08*  (2006.01)
(Continued)

(52) U.S. Cl.
CPC .......... *A61B 8/4466* (2013.01); *A61B 8/4461* (2013.01); *A61B 8/4494* (2013.01);
(Continued)

(58) Field of Classification Search
CPC ..... A61B 8/4461; A61B 8/4494; A61B 8/483; A61B 8/4466; A61B 8/461;
(Continued)

(56) References Cited

U.S. PATENT DOCUMENTS 5,986,972 A * 11/1999 Li ................................. 367/13
6,305,225 B1 * 10/2001 Bae et al. ..................... 73/602
(Continued)

FOREIGN PATENT DOCUMENTS

JP    S57-171255    10/1982
JP    2003-230560   8/2003
(Continued)

OTHER PUBLICATIONS

JPO Office Action issued on Mar. 15, 2016, in counterpart Japanese patent application 2012-086209, with translation.

*Primary Examiner* — Long V Le
*Assistant Examiner* — Katherine McDonald
(74) *Attorney, Agent, or Firm* — Fitzpatrick, Cella, Harper & Scinto

(57) ABSTRACT

Provided is an object information acquiring apparatus including a probe in which a plurality of elements transmitting an ultrasound wave to a measurement target region of an object and receiving a reflected wave is arranged in a first direction, and a mechanical scanning unit that moves the probe in the first direction and a direction crossing the first direction. A transmission processor, to each element included in a transmission aperture element row transmitting the ultrasound wave, inputs an input signal for driving the element, and a received signal processor combines received signals obtained by the elements included in a reception aperture element row receiving the ultrasound wave. A generator generates property information on the object from the combined signal, and a controller that determines at least one of the number of elements included in the transmission aperture element row.

17 Claims, 9 Drawing Sheets

(51) Int. Cl.
*G01S 15/89* (2006.01)
*G01S 7/52* (2006.01)

(52) U.S. Cl.
CPC .......... *A61B 8/483* (2013.01); *G01S 7/52085* (2013.01); *G01S 15/8915* (2013.01); *G01S 15/8945* (2013.01); *A61B 8/461* (2013.01)

(58) Field of Classification Search
CPC ............. G01S 7/52046; G01S 7/52047; G01S 7/52085; G01S 15/8915; G01S 15/8945
USPC .................................................. 600/445, 447
See application file for complete search history.

(56) References Cited

U.S. PATENT DOCUMENTS

2010/0022881 A1* 1/2010 Fujita et al. .................. 600/445
2011/0046484 A1* 2/2011 Adams .......................... 600/440

FOREIGN PATENT DOCUMENTS

| | | |
|---|---|---|
| JP | 2008-073304 | 4/2008 |
| JP | 2009-028366 | 2/2009 |
| WO | 02/30287 A | 4/2002 |

\* cited by examiner

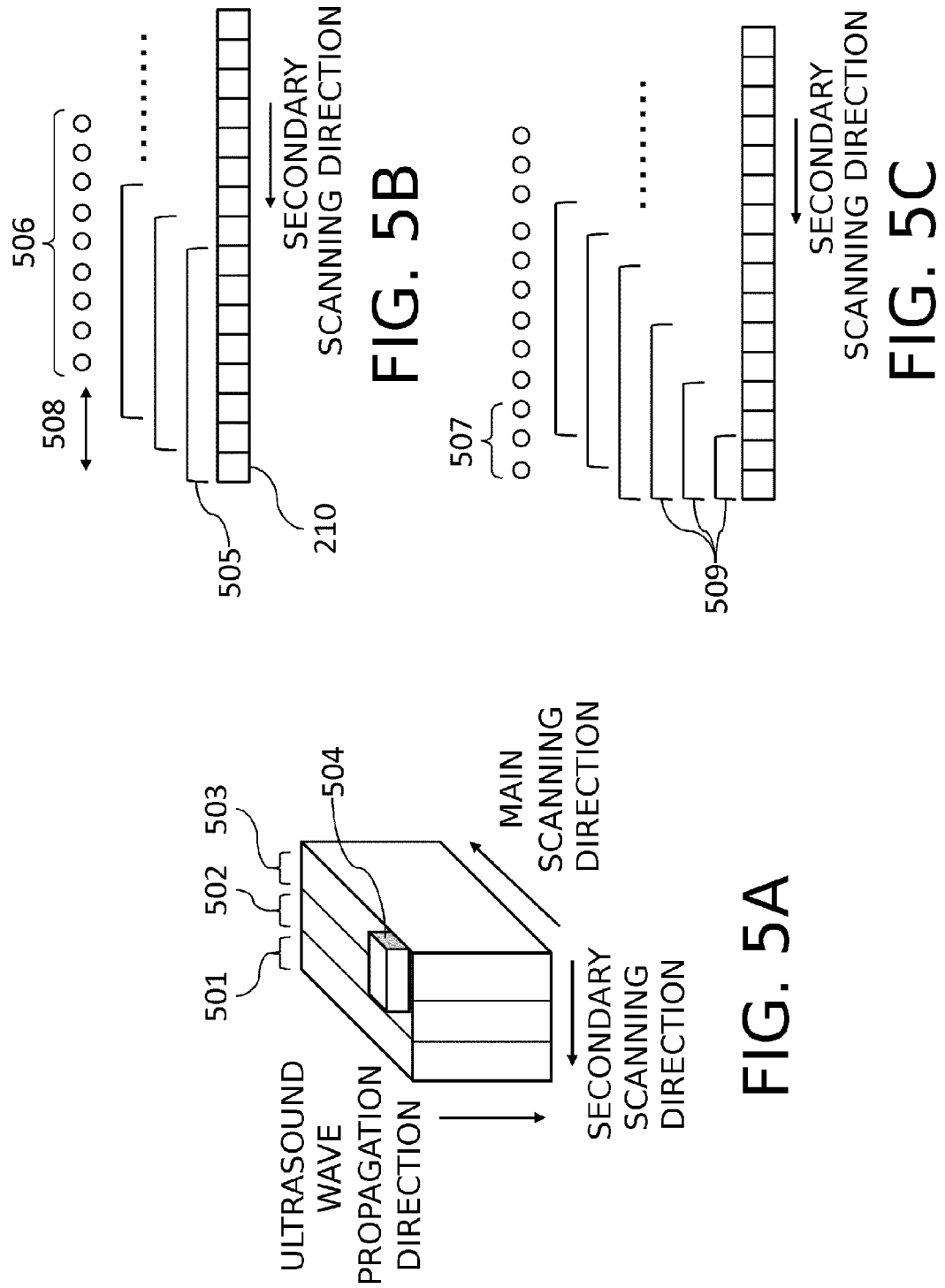

OBJECT INFORMATION ACQUIRING APPARATUS

BACKGROUND OF THE INVENTION

Field of the Invention

The present invention relates to an object information acquiring apparatus.

Description of the Related Art

An apparatus for acquiring object information is known in which an ultrasound beam is transmitted toward an object, a reflected wave from inside the object is received, and the received signal is converted into an image. Japanese Patent Application Laid-Open No. 2009-028366 (Patent Literature 1) discloses a method for generating a three-dimensional ultrasound echo image of a wide region by mechanically scanning a probe in which elements transmitting and receiving ultrasound waves are arranged one-dimensionally. In the apparatus used in this method, a three-dimensional image can be configured by mechanically scanning the probe in a direction crossing the electronic scanning direction, while acquiring tomographic images by electronic scanning of the ultrasound transmitted/received beam. Such a method makes it possible to perform imaging of a three-dimensional region within a wide range of the object in an easy manner and, therefore, is suitable when a wide-range imaging region is required, such as in diagnostic breast imaging.

Patent Literature 1: Japanese Patent Application Laid-Open No. 2009-028366

SUMMARY OF THE INVENTION

When an ultrasound beam is transmitted, a plurality (a preset number) of elements is usually driven to reduce the beam in size. However, with such a method, imaging is impossible with respect to a region in which the preset number of elements cannot be obtained, such as an object region located on the front surface of the end sections of a probe. As a result, the size of the three-dimensional image region becomes less than that of the element surface of the probe. The resultant problem is that even when a wide-range image region is acquired by mechanically scanning the probe, imaging is not performed with respect to the three-dimensional region located on the front surface of the end section of the probe.

The present invention has been created to resolve the above-described problem, and it is an object of the present invention to enlarge the acquired image region in an apparatus that acquires the image of an object by mechanically scanning a probe and transmitting and receiving ultrasound waves.

The present invention provides an object information acquiring apparatus comprising:

a probe in which a plurality of elements transmitting an ultrasound wave to a measurement target region of an object and receiving a reflected wave is arranged in a first direction;

a mechanical scanning unit configured to move the probe in the first direction and a direction crossing the first direction;

a transmission processor configured to input, to each element included in a transmission aperture element row transmitting the ultrasound wave, from among the plurality of elements, an input signal for driving the element;

a received signal processor configured to combine received signals obtained by elements included in a reception aperture element row receiving the ultrasound wave, from among the plurality of elements;

a generator configured to generate property information on the object from the combined received signal; and a controller configured to determine at least one of the number of elements included in the transmission aperture element row, a delay amount of the input signal for each element, the number of elements included in the reception aperture element row, and a delay amount of the received signal for each element, according to a position of the probe in the measurement target region of the object.

In accordance with the present invention, it is possible to enlarge the acquired image region in an apparatus that acquires the image of an object by mechanically scanning a probe and transmitting and receiving ultrasound waves.

Further features of the present invention will become apparent from the following description of exemplary embodiments with reference to the attached drawings.

BRIEF DESCRIPTION OF THE DRAWINGS

FIGS. 5A to 5C illustrate the effects of the present invention in Embodiment 1;

DESCRIPTION OF THE EMBODIMENTS

The effect of the present invention is obtained when the invention is used in an object information acquiring apparatus in which a three-dimensional image is reconstructed by mechanically scanning a probe and using a tomographic image acquired at each position. The object information acquiring apparatus in the present invention, as referred to herein, is an apparatus using ultrasound echo technique by which property information on the interior of the object is acquired as image data by transmitting an ultrasound wave toward the object and receiving the reflected ultrasound wave from the interior of the object. The property information in the present invention is information reflecting the difference in acoustic impedance between the tissues inside the object. The ultrasound wave as referred to in the present invention is a kind of elastic wave inclusive of waves that are called sound wave, ultrasound wave, and acoustic wave.

(Transmitted/Received Beam Forming)

Figure 1A:
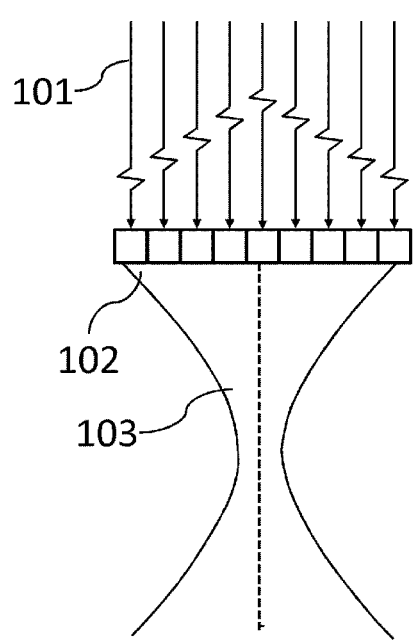
FIGS. 1A and 1B illustrate the principle of beam forming.

The principle of the transmitted/received ultrasound beam formation method will be explained below in a simple manner with reference to FIGS. 1A and 1B. Beam formation during ultrasound wave transmission is called transmitted beam forming, and beam formation during ultrasound wave reception is called received beam forming. As shown in FIG. 1A, in the transmitted beam forming, each transducer element of a transmission aperture element row 102 is driven by a delayed input signal 101, and a beam 103 is finely focused in a certain location and transmitted.

Figure 1B:
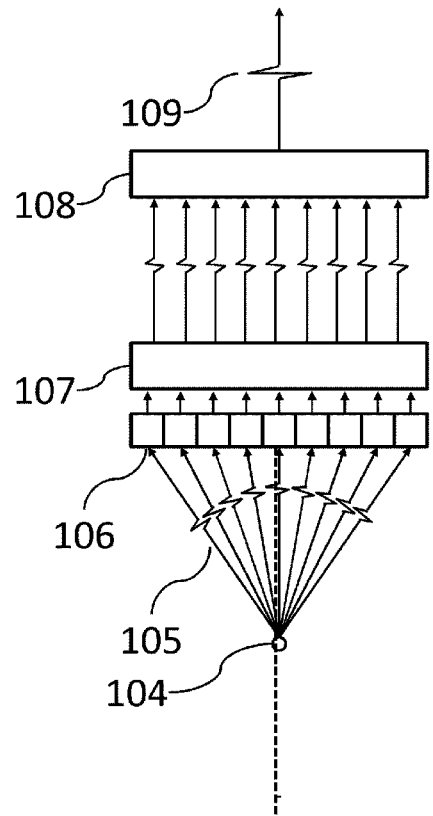

FIG. 1B shows how the received beam forming is performed with respect to a signal obtained by receiving an ultrasound wave 105 reflected by a point reflector 104 with each transducer element of the reception aperture element row 106. In the received beam forming, the received signals of the elements are delayed with a delay device 107 and then combined into a combined output signal 109 by a combined signal generator 108. As a result, a signal produced by selective augmentation of a reflective signal at any location can be obtained.

In the configuration shown in FIG. 1, the number of transmission aperture elements is equal to that of reception aperture elements, but those numbers may actually be different. In the explanation below, it is assumed that the transmission aperture element row and the reception aperture element row are the same element row, and those elements are commonly referred to as "aperture elements". A region formed by the aperture elements is called the "aperture".

The combined output signal 109 is obtained by implementing the reception beam forming with respect to the received ultrasound wave. The combined output signal 109 is an ultrasound echo signal reflecting time sequence changes of the intensity of reflected ultrasound wave that correspond to the difference in acoustic impedance on a scanning line (the dashed lines in FIGS. 1A and 1B). The position of the scanning line at which the ultrasound echo signal is obtained in this case is on the inner side (in the figure, substantially in the center of the aperture) of the width of the aperture elements, and a region that is narrower than the entire aperture width is obtained.

An ultrasound echo signal on the scanning line in the aperture center can be obtained by setting the aperture on a transducer in which a plurality of transducer elements are arranged one-dimensionally and performing the transmission/reception beam forming with respect to the aperture elements constituting the aperture. By changing the combination of the aperture elements constituting the aperture, it is possible to obtain a sequence of ultrasound echo signals on the scanning lines arranged substantially parallel to each other. The combination of the aperture elements is changed, for example, by offsetting the elements constituting the aperture on the transducer array by one element or a predetermined number of elements.

As a result, a tomographic image corresponding to the two-dimensional distribution of acoustic impedance can be acquired. Such a process of moving the aperture on the transducer array and scanning the scanning line is called electronic scanning. In this case, a set of constant delay amounts (called "delay pattern") is imparted to each element in the aperture to perform the transmission/reception beam forming (Area where Image Cannot be Formed)

When electronic scanning is performed, tomographic images in the region corresponding to the width of the elements arranged in the transducer array can be expected to be acquired. However, actually, where electronic scanning is performed without changing the number of aperture elements, the scanning range of the scanning line becomes narrower than the width (in the element arrangement direction) of the transducer array. This is because the scanning line cannot be formed in the end sections of the arranged elements, since the scanning line is substantially in the center of the aperture.

As a result, even when the probe is scanned mechanically and a three-dimensional image is generated by combining the tomographic images acquired by electronic scanning, the actual image acquisition region becomes smaller than the mechanical scanning region of the probe. In particular, the region in which image acquisition is impossible appears when the range scannable by mechanical scanning is restricted by the probe shape.

With respect to the region in which image acquisition is impossible with the usual aperture movement, as mentioned hereinabove, a method has been considered by which a scanning line is formed by changing the number of the elements included in the aperture or the delay pattern imparted to each element.

There is a method for reducing the number of the elements included in the aperture in the end section of the transducer array. Thus, the number of aperture elements is changed according to the position in the transducer array during electronic scanning, and the number of elements in the aperture in the end section is reduced. As a result, the scanning range of the scanning line can be enlarged. In this case, the delay pattern imparted to each element in the aperture is changed according to the numerical aperture, and where the settings ensure symmetrical arrangement with respect to the aperture center at all times, the scanning line is positioned in the aperture center.

With another method, the scanning line is set at a position displaced from the position of a line perpendicular substantially to the center of the aperture element row by using a delay pattern that is asymmetrical with respect to the aperture center for imparting to each aperture element. Where the delay pattern is thus made asymmetrical, the scanning line can be formed in the end section of the transducer array, without changing the numerical aperture. As a result, the measurement region can be enlarged.

The delay pattern may be also provided asymmetrically with respect to the aperture center, while changing the number of aperture elements. Where the scanning line is set to a position displaced from the position of a line perpendicular substantially to the center of the aperture element row, while changing the number of aperture elements, the scanning line can be also formed in the end section of the transducer array and the measurement region can be enlarged.

However, in the method of changing the numerical aperture, the thickness of the ultrasound beam formed in the transmission/reception beam forming is changed and the spatial resolution of the ultrasound echo signal is also changed. Further, with the method by which the relative distance or angle of the scanning line from the position substantially in the center of the aperture element row is changed by changing the delay pattern, the spacing of the scanning lines and spatial resolution vary depending on the depth. Therefore, where those parameters are changed in the course of electronic scanning, the resolution of tomographic images is partially changed.

In accordance with the present invention, the region in which the resolution varies is reduced, while enlarging the image acquisition region, by changing the control pattern (numerical aperture and delay pattern) during electronic scanning according to the mechanical scanning position of the probe.

The preferred embodiment of the present invention will be described below with reference to the appended drawings. The dimensions, materials, shapes and mutual arrangement of constituent components described below can be changed, as appropriate, according to various conditions or the configuration of the apparatus using the present invention, and the scope of the present invention should not be construed as being limited to the following description.

Embodiment 1

Configuration of the Apparatus

Figure 2:
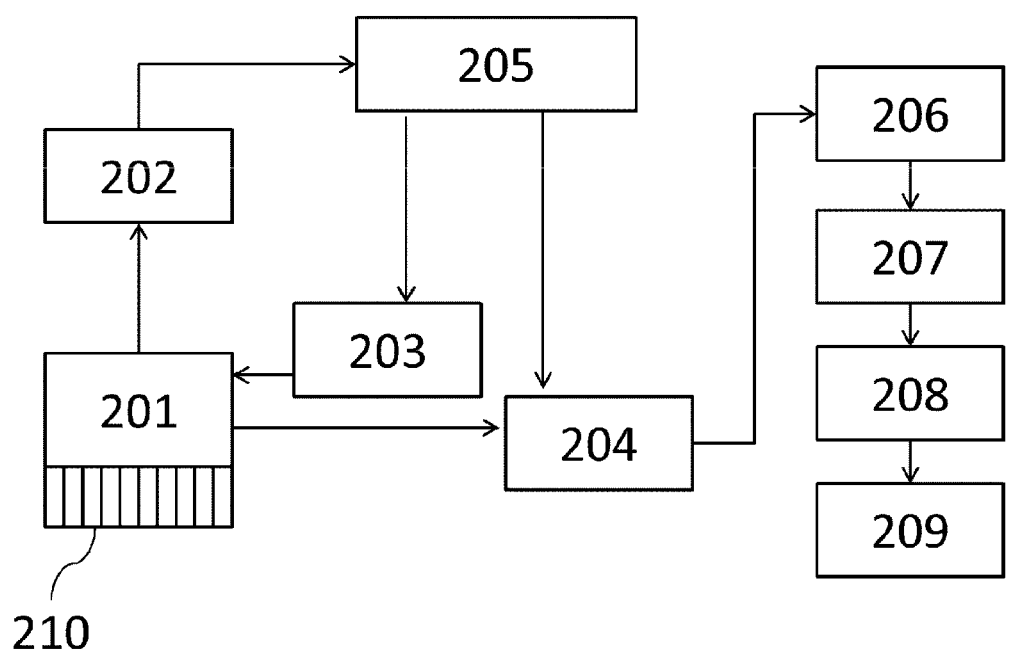
FIG. 2 shows the configuration of the apparatus of Embodiment 1.

FIG. 2 shows the configuration of the object information acquiring apparatus in accordance with the present invention. The apparatus is provided with a probe 201, a mechanical scanning mechanism 202 for the probe, a transmitting processing unit 203, a received signal processing unit 204, a control unit 205, an image processing unit 206, an image memory 207, an image reconstruction unit 208, and an image display unit 209. A transducer array 210 with one-dimensional arrangement of elements is provided on the probe 201.

As mentioned hereinabove, an ultrasound transmission/reception beam from the aperture elements on the transducer array 210 is electronically scanned over a tomographic surface and a tomographic image is produced. The probe 201 is fixed to a movable section of the mechanical scanning mechanism 202 and moves together with the movable section. The transmitting processing unit 203 switches aperture elements that are to be driven, generates an input signal and forms a transmission ultrasound beam. The transmitting processing unit corresponds to the transmission processor in accordance with the present invention. The received signal processing unit 204 adds and combines the delayed received signals of each aperture element, thereby forming a reception ultrasound beam and outputting an ultrasound echo signal for each scanning line. The received signal processing unit corresponds to the received signal processor in accordance with the present invention. In order to pick up tomographic images, the ultrasound transmission/reception beam is electronically scanned by switching the drive element for each scanning line in the transducer array 210.

The image processing unit 206 subjects the ultrasound echo signal to complex signal conversion, performs LOG compression and adjustment such as gain adjustment, and produces and outputs an image signal. The control unit 205 controls the number of aperture elements in electronic scanning and the delay pattern according to the mechanical scanning of the probe. More specifically, the transmission aperture elements, delay pattern of the input signal, reception aperture elements, and delay pattern of the received signal are determined and outputted to the transmitting processing unit 203 and the received signal processing unit 204 according to the aperture position of electronic scanning. The control unit corresponds to the controller in accordance with the present invention. The specific feature of the present embodiment is that the combination of the numerical aperture and delay pattern inputted to the transmitting processing unit 203 and the received signal processing unit 204 according to the electronic scanning is changed according to the mechanical scanning of the probe.

The image signal obtained for each electronic scanning is stored in the image memory 207 as a signal forming one tomographic image. The tomographic images are acquired, while moving the probe 201, and the acquired tomographic images are successively stored in the image memory 207. The stored tomographic images are reconstructed as a three-dimensional image in the image reconstruction unit 208, and the reconstructed image is outputted to the image display unit 209. In accordance with the present invention, it is not always necessary to provide the image reconstruction unit 208 and the image display unit 209. Thus, the configuration can be also used in which the acquired tomographic images and the three-dimensional image are recorded in an external memory and the image reconstruction processing and display are performed in an off-line mode.

(Mechanical Scanning)

Figure 3:
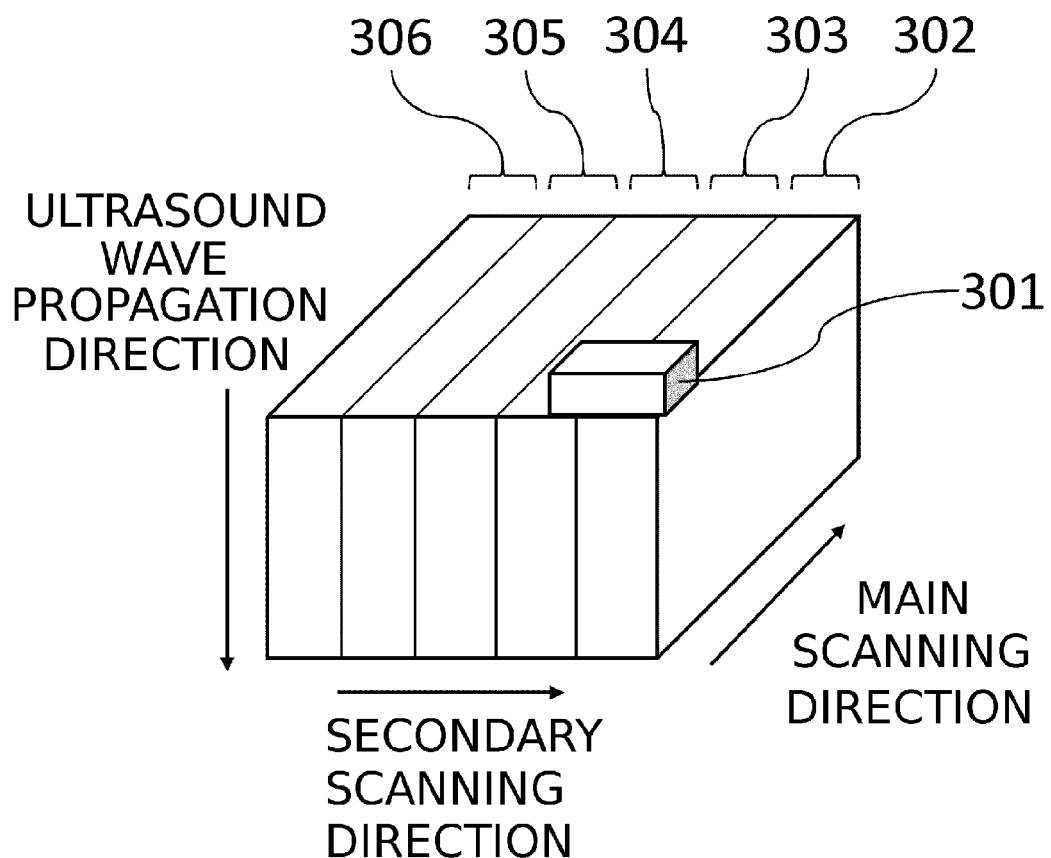
FIG. 3 illustrates a three-dimensional image region obtained by mechanical scanning in Embodiment 1.

The mechanical scanning method of the present embodiment will be explained below. FIG. 3 is a conceptual diagram representing a three-dimensional image region obtained by mechanically scanning the probe 301. First, at a position 302, the probe is mechanically scanned in the main scanning direction, while acquiring the tomographic images. Then, the probe 301 is moved to a position 303 in the secondary scanning direction. A three-dimensional image is acquired by repeating the aforementioned main scanning in a similar manner at secondary scanning positions 303, 304, 305, and 306. In this case, the secondary scanning direction is the arrangement direction of the elements and will also be referred to as the first direction. The main scanning direction crosses the first direction and is preferably orthogonal thereto. However, the main scanning of each stripe (each secondary scanning position) may be performed a plurality of times. As a result, the SN ratio is increased. Further, in the adjacent stripe after one-cycle secondary scanning, the probe may be subjected to main scanning in the direction opposite to the direction of the main scanning performed, while acquiring the tomographic image.

(Control Flow)

Figure 4:
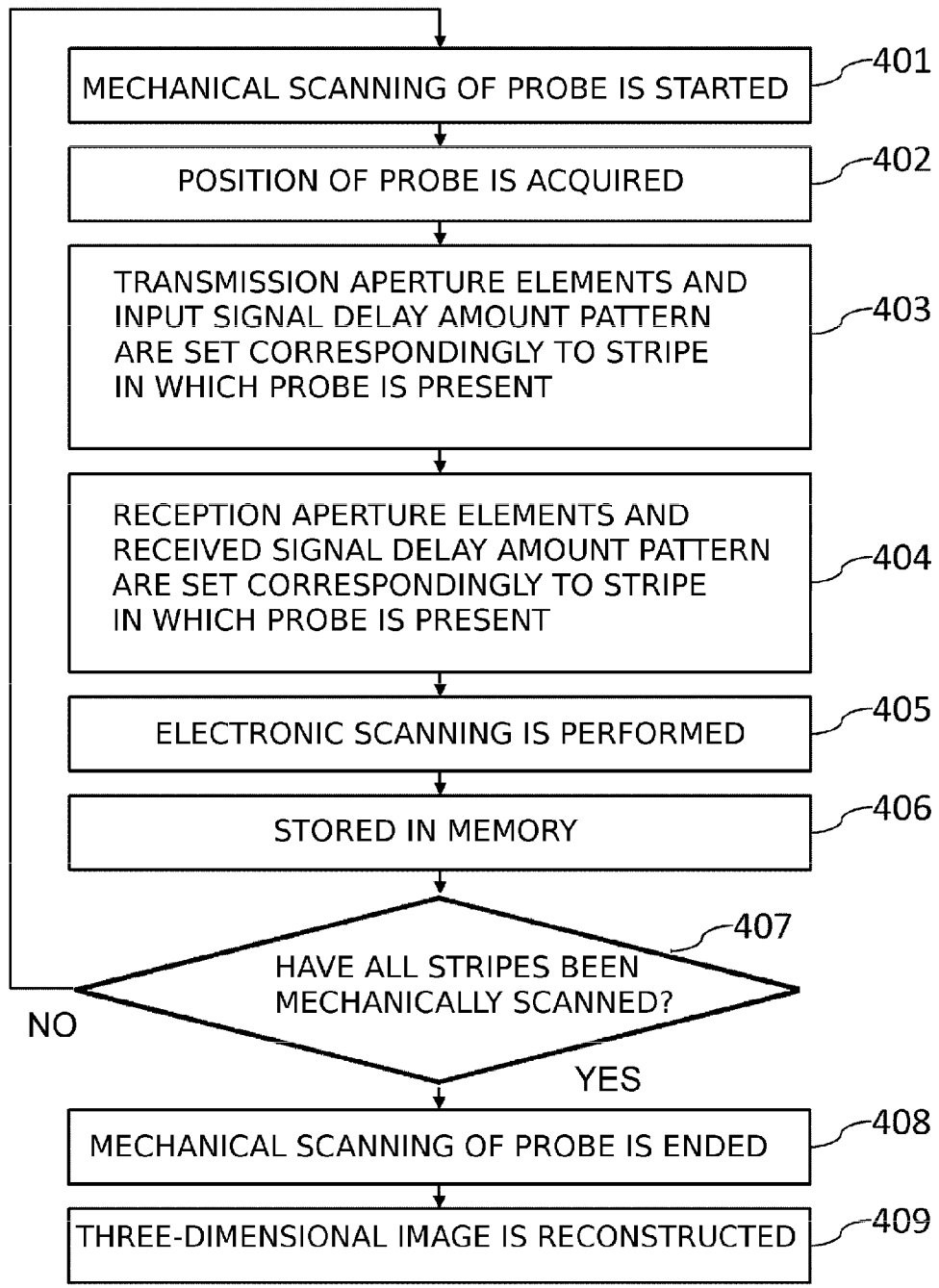
FIG. 4 illustrates the flow of the control method in Embodiment 1.

The control flow of the present embodiment will be explained below with reference to FIG. 4. A three-dimensional image region obtained by main scanning in each stripe is defined as a stripe region. The main scanning direction is the longitudinal direction of the stripe region, and the secondary scanning direction is the direction in which the probe is moved between the stripe regions.

In step 401, mechanical scanning is started from the state in which the probe is disposed at a desired position. In step 402, the probe position is acquired by the mechanical scanning mechanism 202. Where the probe position in the mechanism is known, the relative mutual arrangement of the object and the probe can be identified. In other words, it can be determined whether or not the probe is at a special position such as the end section of the object.

In step 403, an element row (transmission aperture element row) selected as a transmission aperture in a transmissive processing unit and a delay amount pattern imparted to the input signal inputted to the element row are set according to the stripe region in which the probe is present. Likewise, in step 404, an element row (reception aperture element row) selected as a reception aperture in a receiving processing unit and a delay amount pattern imparted to the received signals in the element row are set according to the stripe region in which the probe is present. As mentioned above, those delay amount patterns change as the mechanical scanning advances. For this reason, the control pattern (aperture elements and delay amount pattern) in each stripe region is stored in advance in the control unit 205.

In step 405 and step 406, electronic scanning is performed using the control pattern (transmission aperture element row or reception aperture element row, and delay amount pattern). A tomographic image is then acquired on the basis of the reflected wave and stored in a memory. At this stage, the intensity of the ultrasound wave may be stored in a memory in association with the element position or delay amount and eventually the necessary data may be read out and converted into an image, without producing the tomographic image. Where a stripe region where the measurements still should be conducted remains in the measurement target region of the object (step 407=NO), the probe is moved by secondary scanning. Electronic scanning corresponding to the positional relationship with the object after this movement is then performed, property information on the object is acquired, and the mechanical scanning of the probe is continued, while storing the tomographic image in the memory. Meanwhile, where the acquisition of information with respect to all of the stripe regions included in the measurement target region in the object has been completed (step 407=YES), the mechanical scanning is ended in step 408. In step 409, the three-dimensional image of the object is reconstructed.

(Method for Enlarging Information Acquisition Area)

A method for enlarging the three-dimensional image region will be explained below with reference to FIG. 5. In the present embodiment, it is assumed that the region in which the mechanical scanning mechanism 202 can move the probe by secondary scanning (measurement target region) is set in advance. The number of scanning cycles in the main scanning and the number of secondary scanning cycles in the secondary scanning are set at the same time.

FIG. 5 illustrates an example in which three stripes are present in the measurement target region. FIG. 5A illustrates the mechanical scanning. It is assumed that the secondary scanning is performed in stripes 503, 502, and 501 in the order of description. The stripe 501 is the end section of the object, the stripe 503 is not the end section of the object, the other stripes (not shown in the figure) are present adjacently thereto. The electronic scanning illustrated by FIGS. 5B and 5C is performed according to the positional relationship of the object and probe in such mechanical scanning FIG. 5B illustrates schematically the electronic scanning when the probe 504 performs the main scanning of the stripes 502 and 503. In such main scanning, the same delay pattern is used in all of the electronic scanning cycles. The reference numeral 505 stands for an aperture form, and the reference numeral 506 stands for a scanning line position. For example, the scanning line at the left end is formed from the aperture at the left end. The aperture 505 is produced by selecting a plurality of elements from the transducer array 210. The tomographic images are acquired by electronically scanning the aperture element row 505. In this case, the number of aperture elements is 8. In the electronic scanning performed at this time, a non-imaging region 508 is generated in the direction of secondary scanning In the present embodiment, the movement of the probe in the secondary scanning direction is used with respect to the non-imaging region 508 in the stripe which is not the end section of the measurement target region, such as the stripe 502 or 503. More specifically, during secondary scanning from the stripe 503 to the stripe 502 and during secondary scanning from the stripe 502 to the stripe 501, the probe scanning overlaps the position of the non-imaging region. For example, in the secondary scanning, the probe is moved through the distance equal to the half of the stripe and then the next main scanning is performed. As a result, the transmission/reception of the ultrasound wave can be also performed by the preset number of aperture elements with respect to the non-imaging region 508. In this case, the stripes can be also considered as overlapping.

The movement distance in the secondary scanning serving to enable imaging in the non-imaging region is not limited to that mentioned hereinabove. For example, where the SN ratio is increased by performing measurements a plurality of times with respect to each location in the measurement target region, the gapless transmission/reception of ultrasound waves can be also performed by slightly shifting the position at which the main scanning is performed.

The transmission/reception of ultrasound wave and the generation of image based on the received reflected wave can be performed as a continuous process or separately. When those operations are performed separately, all of the acquired positions and intensities of the reflected waves corresponding to the transmitted ultrasound wave are stored in the memory, and the necessary data may be selected on the basis of the distance between the elements and the position in the object that is to be reconstructed in subsequent image reconstruction.

FIG. 5C is a schematic diagram of electronic scanning in the final stripe region (501) of mechanical scanning. In this case, the numerical aperture and delay pattern are changed according to the position of electronic scanning. The reference numeral 509 denotes the mode of changing the numerical aperture in this case, and the reference numeral 507 represents the position of the scanning line corresponding to each aperture.

In the case illustrated by the figure, the number of aperture elements 509 is reduced by comparison with the usual set number (8) in the end section of the stripe (that is, at a position where subsequent mechanical scanning is impossible) in order to acquire a scanning line signal of the non-imaging region 508. For example, the aperture 509 at the left end in the figure is constituted by two elements, and the ultrasound beam is transmitted and received along the scanning line 507 at the left end. Thus, the control unit 205 changes the aperture element row and delay pattern according to the scanning line formation position. The scanning line is not restricted to a position substantially in the center of the aperture element row, and the desired effect can be also attained by setting the scanning line to a position shifted from the position of a line perpendicular to a position substantially in the center of the aperture element row, while changing the number of elements.

The above-described processing operations are performed independently for the transmission aperture and reception aperture, and different numbers of elements and delay patterns may be selected therefor.

Figure 6A:
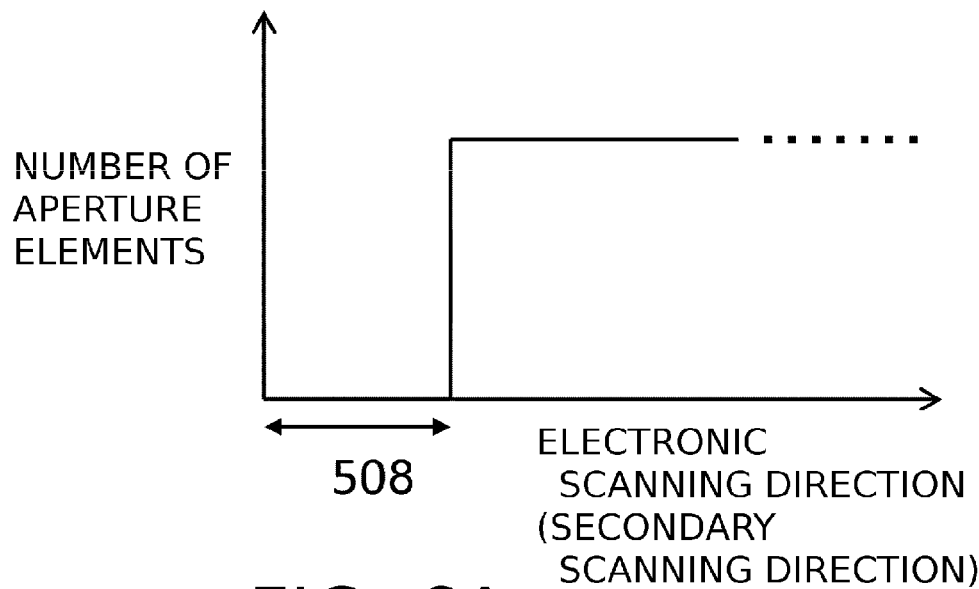
FIGS. 6A and 6B illustrate the relationship between a numerical aperture and a position in the electronic scanning direction in Embodiment 1.
Figure 6B:
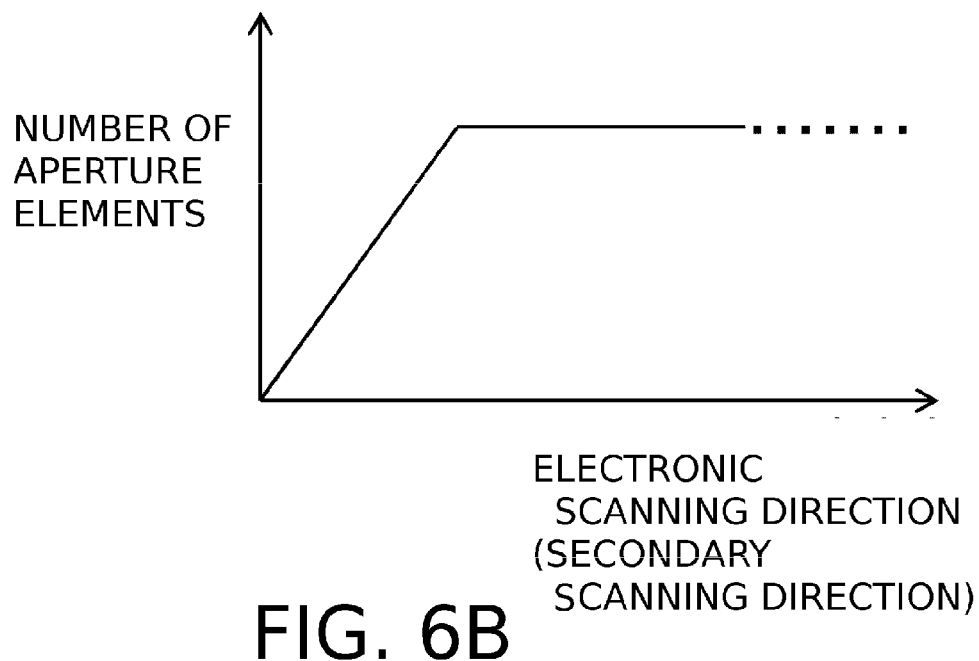

FIG. 6 is a conceptual diagram illustrating changes in the number of aperture elements between the scanning lines in the above-described control method. FIGS. 6A and 6B correspond to FIGS. 5B and 5C, respectively. In FIG. 6A, in the portion corresponding to the non-imaging region 508, no aperture is formed, and an aperture is formed after the electronic scanning moves to a range in which the preset numerical aperture can be realized. In this case, property information is acquired by adjusting the secondary scanning distance with respect to the portion in which forming has not been performed. Meanwhile, in the case illustrated by FIG. 6B, since subsequent secondary scanning cannot be performed, an aperture is formed by reducing the number of elements even if the resolution has changed.

Effects of the Invention

By switching the control method of the transmissive processing unit and received signal processing unit in the above-described manner, it is possible to reconstruct a three-dimensional image with an enlarged image region, while reducing the region in which the resolution changes.

In this case, the enlargement of the image region is realized with respect to portions (stripes 502 and 503) other than the end section of the measurement target region by moving the probe during the secondary scanning and performing the transmission/reception of ultrasound wave in the non-imaging region. The image region in the end section (stripe 501) of the measurement target region is enlarged by reducing the number of elements forming the aperture and enlarging the scanning line.

The region in which the resolution varies is reduced by restricting the region in which the scanning line is formed by a small number of aperture elements to an end portion (507 in FIG. 5C) of the stripe (501) in the end section of the object. In other words, in the stripes (502, 503) other than the end section of the measurement target region, the ultrasound wave transmission/reception is performed by using secondary scanning, without reducing the number of aperture elements even in the non-imaging region. Generally, where the number of aperture elements is small, the intensity of ultrasound wave decreases and the SN ratio decreases, but with the method of the present invention such effects can be avoided.

Where the probe is positioned outside the stripe 501, the scanning line obtained in one cycle of electronic scanning decreases in size. Therefore, the amount of data transferred into the image memory per one tomographic image can be reduced.

In the above-described process, the stripes 503, 502, and 501 are secondary scanned in the order of description, but where the control of the aperture number and delay pattern in the electronic scanning of each stripe region and the position of mechanical scanning of the probe in the secondary scanning direction are set as described hereinabove, the order of secondary scanning may be reversed.

The effects obtained are explained below by using a probe for linear electronic scanning as an example of the above-mentioned probe.

The following conditions are assumed: number of aperture elements N=64 [ch], element pitch d=0.3 [mm], elevation direction distance of mechanical scanning le=200 [mm], and acoustic propagation direction distance of tomographic image lp=50 [mm]

In this case, the size of the region enlarged in the present embodiment is d×(N−1)/2 (decimal point truncation)×le×lp. Therefore, the three-dimensional image is enlarged by about 9 [mm]×200 [mm]×50 [mm]

Embodiment 2

In the method explained in Embodiment 1, the number of aperture elements is changed in order to enlarge the imaging region in the secondary scanning direction in the end section of the mechanically scannable range (the end portion of the measurement target region of the object).

In the present embodiment, by contrast with Embodiment 1, when the probe is positioned in the end section of the secondary scanning range (stripe), the transmitted/received ultrasound beam is deflected to enlarge the tomographic image region.

Figure 7A:
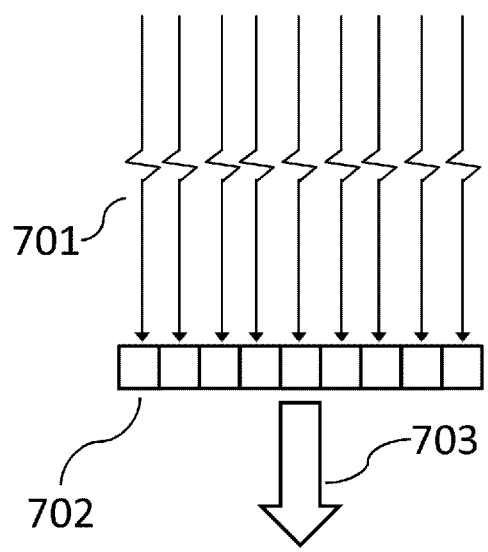
FIGS. 7A and 7B illustrate a method for electronically deflecting a transmitted ultrasound beam.

FIG. 7 is a conceptual diagram of an input signal for deflecting the transmitted beam. As shown in FIG. 7A, where a pulse signal 701 is inputted into each element of the transmission aperture element row 702 at the same timing, the transmitted ultrasound beam is formed in a direction 703 orthogonal to the element arrangement direction in the transmission aperture element row 702. A position for converging the ultrasound wave can be also set by providing a delay for each element of the transmission aperture element row 702 in a form that is axially symmetrical with respect to the central element as an axis.

Figure 7B:
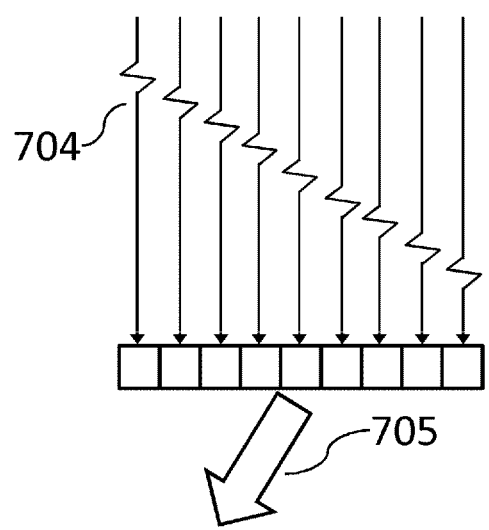

Meanwhile, in the configuration shown in FIG. 7B, the delay pattern of an inputted pulse signal 704 is changed asymmetrically. As a result, the transmitted ultrasound beam can be deflected from the direction 703 shown in FIG. 7A in a direction 705 forming a predetermined angle therewith. Likewise, the received ultrasound beam can be also deflected by adequately delaying the received signals before the received signals are combined.

Figure 8:
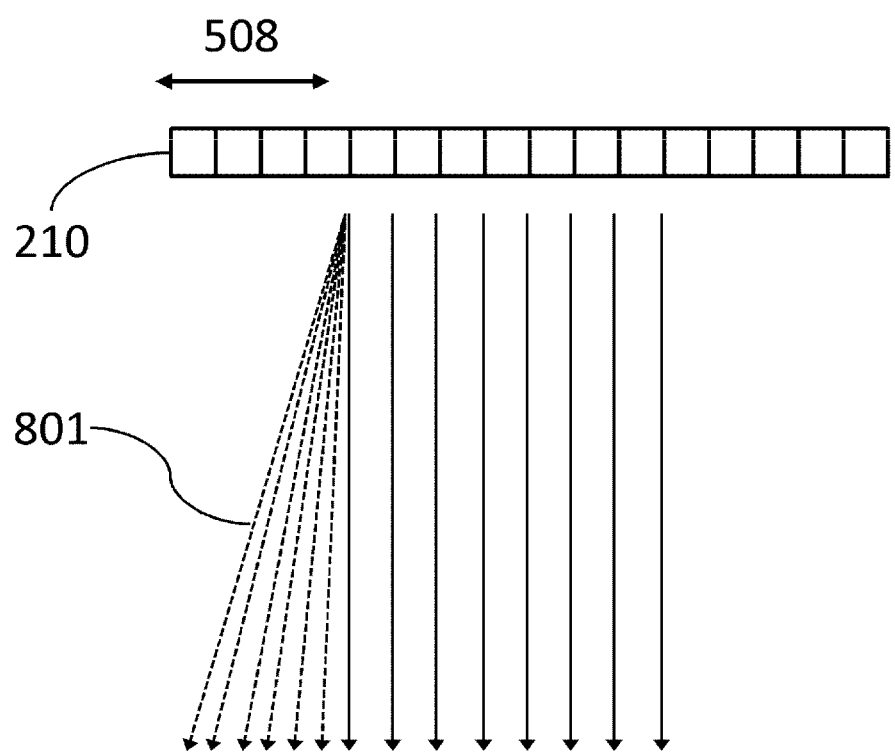
FIG. 8 illustrates a scanning line signal acquired in Embodiment 2.

FIG. 8 is a conceptual diagram illustrating the transmission/reception mode of the deflected ultrasound beams with respect to the end portion of the secondary scanning range (stripe) in the measurement target region. A deflected scanning line 801 is formed with respect to the non-imaging region 508. In order to deflect the scanning line in such a manner, the delay pattern of the pulse signal inputted from the control unit 205 and the delay pattern of the received signal may be changed with respect to the aperture element row of the arrangement end section of the transducer array 210.

In the present embodiment, by contrast with Embodiment 1, it is not necessary to reduce the number of aperture elements. Further, the scanning line signal may be acquired in a range wider than the non-imaging region 508 in the secondary scanning direction by broadly deflecting the ultrasound transmitted/received beam.

Embodiment 3

In the present embodiment, the mechanical scanning range of the probe is not set at the apparatus side, and an examiner determines the desired mechanical scanning range (examiner's setting range) by using input means.

Displaying the object picked up with a camera at the image and indicating the examiner's setting range on the image can be used as the input means for the examiner's setting range. The image pickup means is not limited to the camera and other medical diagnostic devices may be also used.

Figure 9:
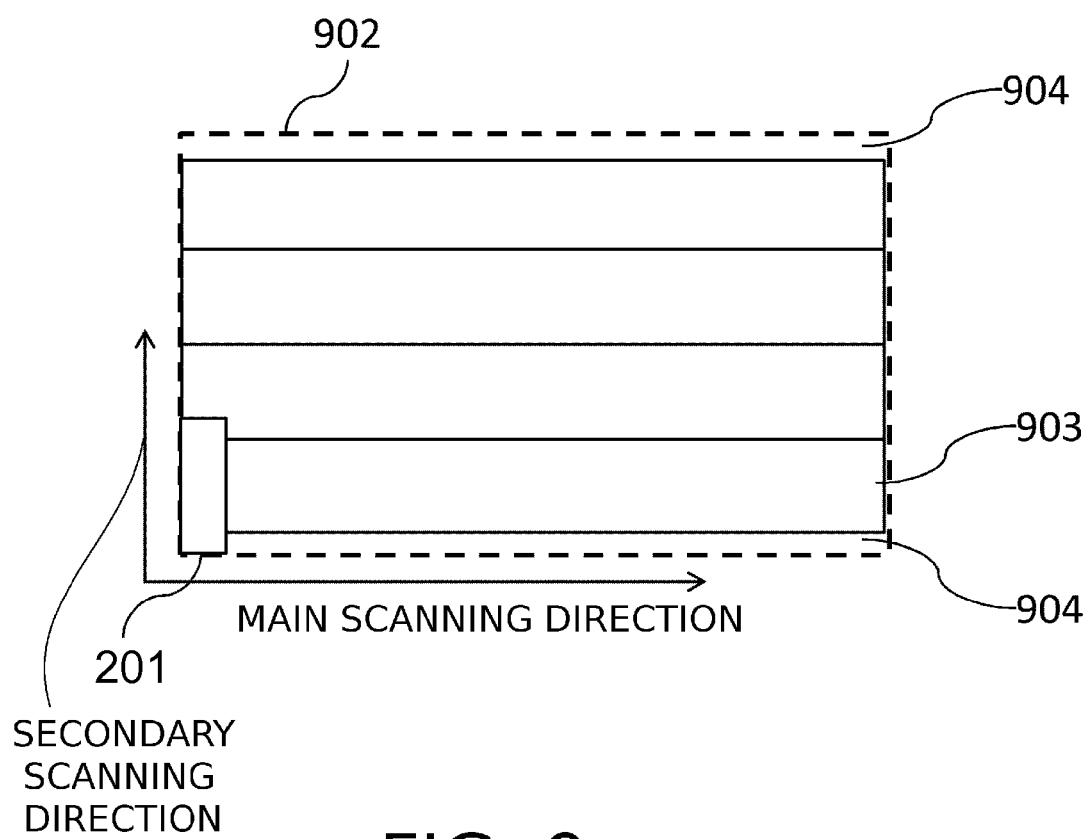
FIG. 9 illustrates the mechanical scanning range of the probe in Embodiment 3.

FIG. 9 is a conceptual diagram illustrating the relationship of image regions acquired by mechanical scanning of an examiner's setting range 902 and the probe 201 (901). A stripe region 903 is superimposed on the examiner's setting range 902 by mechanically scanning the probe 201 in the main scanning direction and secondary scanning direction in the same manner as in Embodiment 1. In this case, a non-imaging stripe region 904 is generated in the mechanical scanning range of the probe. The non-imaging stripe region 904 can be picked up by changing the method for controlling the transmissive processing unit 203 and the received signal processing unit 204 from the control unit 205 in the same manner as in Embodiment 1 or Embodiment 2.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-086209, filed on Apr. 5, 2012, which is hereby incorporated by reference herein in its entirety.

What is claimed is:
1. An object information acquiring apparatus comprising:
    a probe in which a plurality of elements are arrayed in a first direction, wherein said plurality of elements perform electronic scanning by transmitting an ultrasound wave to a measurement target region of an object and receiving a reflected wave;
    a mechanical scanner arranged to position said probe in a scanning movement in said first direction and in a direction crossing said first direction, wherein each movement in said first direction forms a stripe;

a transmission beam former which inputs, to each element included in a transmission aperture element row transmitting the ultrasound wave, from among said plurality of elements, an input signal for driving the element;

a received signal beam former which combines received signals obtained by elements included in a reception aperture element row receiving the ultrasound wave, from among said plurality of elements;

a generator which generates property information on the object from the combined received signal; and a controller which gradually reduces the number of elements included in the transmission aperture element row or the number of elements included in the reception aperture element row in the electronic scan as the position of said probe comes to the stripe on an end section of the measurement target region of the object, such that with respect to the elements included in the transmission aperture row or the reception aperture row, a center of the elements shifts within the array in a direction to the end section of the measurement target region as the position of said probe comes to the stripe on the end section.

2. The object information acquiring apparatus according to claim 1, wherein said mechanical scanner causes said probe to perform main scanning in said direction crossing said first direction and secondary scanning in said first direction.

3. The object information acquiring apparatus according to claim 2, wherein when a position of said probe in the main scanning includes an end section of the measurement target region of the object, said controller determines the delay amount of the input signal or the received signal for each element so that a deflected ultrasound wave is transmitted or received in the end section of the measurement target region of the object.

4. The object information acquiring apparatus according to claim 2, wherein when a position of said probe in the main scanning does not include an end section of the measurement target region of the object, said mechanical scanner causes said probe to perform the secondary scanning such that a region through which said probe moves in the main scanning has a portion overlapping in said first direction.

5. The object information acquiring apparatus according to claim 1, further comprising:
an input unit which accepts an input of the measurement target region of the object obtained by said probe.

6. An object information acquiring apparatus comprising:
a probe in which a plurality of elements are arrayed in a first direction, wherein said plurality of elements perform electronic scan by transmitting an ultrasound wave to a measurement target region of an object and receiving a reflected wave;
a mechanical scanner arranged to position said probe in a scanning movement in said first direction and in a direction crossing said first direction, wherein each movement in said first direction forms a stripe;
a transmission beam former which inputs, to each element included in a transmission aperture element row transmitting the ultrasound wave, from among said plurality of elements, an input signal for driving the element;
a received signal beam former which combines received signals obtained by elements included in a reception aperture element row receiving the ultrasound wave, from among said plurality of elements;

a generator which generates property information on the object from the combined received signal; and a controller which changes the number of elements included in the transmission aperture element row or the number of elements included in the reception aperture element row, and which changes a delay amount of the input signal for each element or a delay amount of the received signal for each element in the electronic scan, as the position of said probe comes to the stripe on an end section of the measurement target region of the object, such that with respect to the elements included in the transmission aperture row or the reception aperture row, a center of the elements shifts within the array in a direction to the end section of the measurement target region as the position of said probe comes to the stripe on the end section, and such that a direction of a transmission beam is shifted toward the end section of the measurement target region.

7. The object information acquiring apparatus according to claim 6, wherein said controller gradually decreases the number of elements included in the transmission aperture element row or the number of elements included in the reception aperture element row, as the position of said probe comes to the stripe on the end section of the measurement target region of the object.

8. The object information acquiring apparatus according to claim 6, wherein said controller changes the delay amount of the input signal for each element or the delay amount of the received signal for each element, in order to form a scanning line at a location of a center of a plurality of elements included in the reception aperture element row.

9. The object information acquiring apparatus according to claim 6, wherein said controller changes the delay amount of the input signal for each element or the delay amount of the received signal for each element, in order to form a scanning line at a location out of center of a plurality of the elements included in the reception aperture element row.

10. The object information acquiring apparatus according to claim 1, wherein said controller maintains constant the number of elements included in the transmission aperture element row or the number of elements included in the reception aperture element row when the position of said probe is not on the stripe on the end section of the measurement target region of the object.

11. The object information acquiring apparatus according to claim 10, wherein said generator generates the property information on a non-imaging region of the object by using the received signals obtained by the scanning movement in the direction crossing said first direction when the position of said probe is not on the stripe on the end section of the measurement target region of the object.

12. The object information acquiring apparatus according to claim 6, wherein said controller maintains constant the number of elements included in the transmission aperture element row or the number of elements included in the reception aperture element row when the position of said probe is not on the stripe on the end section of the measurement target region of the object.

13. The object information acquiring apparatus according to claim 12, wherein said generator generates the property information on a non-imaging region of the object by using the received signals obtained by the scanning movement in the direction crossing said first direction when the position of said probe is not on the stripe on the end section of the measurement target region of the object.

14. An object information acquiring apparatus comprising:
- a probe having a plurality of elements arranged in an array along a first direction, wherein each of said elements transmits and receives an acoustic wave;
- a scanning unit which moves said probe in the first direction, the probe being moved within a measurement region; and
- a controller which controls said plurality of elements to change at least one of:
  - (A) a reception aperture, such that, in a case in which said probe is moved within the measurement region and moved to an end portion of the measurement region, first transducers in an end portion of said array closer to the end portion of the measurement region are included in the reception aperture while a second transducer in a portion of said array located further from the end portion than the first transducers is omitted from the reception aperture,
  - (B) a transmission aperture, such that, in a case in which said probe is moved within the measurement region and moved to an end portion of the measurement region, first transducers in an end portion of said array closer to the end portion of the measurement region are included in the transmission aperture while a second transducer in a portion of said array located further from the end portion than the first transducers is omitted from the transmission aperture,
  - (C) a delay amount of received signals output from elements included in the reception aperture such that, in a case in which said probe is moved within the measurement region and moved to an end portion of the measurement region, a scanning line is formed in a direction offset from the direction normal to said array, and
  - (D) a delay amount of transmission signals input to elements included in the transmission aperture such that, in a case in which said probe is moved within the measurement region and moved to an end portion of the measurement region a scanning line is formed in a direction offset from the direction normal to said array.

15. The object information acquiring apparatus according to claim 14, wherein said scanning unit moves said probe in a second direction crossing said first direction.

16. The object information acquiring apparatus according to claim 14, wherein said controller controls said plurality of elements to change the reception aperture, such that, in a case in which said probe is not positioned at the fringe of the measurement region, elements in the end portion and the portion away from the end portion are included in the reception aperture.

17. An object information acquiring apparatus comprising:
- a probe having a plurality of elements arranged in an array along a first direction;
- a scanning unit which moves said probe in the first direction, the probe being moved within a measurement region; and
- a controller which performs at least one of:
  - (A) reception beam-forming such that the number of said elements used for forming a first scanning line is smaller than the number of said elements used for forming a second scanning line formed further from the end portion of the measurement region than the first scanning line, and
  - (B) transmission beam-forming such that the number of said elements used for forming a first scanning line is smaller than the number of said elements used for forming a second scanning line formed further from the end portion of the measurement region than the first scanning line.

* * * * *